(12) United States Patent
D'Amato et al.

(10) Patent No.: US 12,208,139 B2
(45) Date of Patent: *Jan. 28, 2025

(54) CONTROLLED DRUG RELEASE FROM ELECTROSPUN FIBERS

(71) Applicant: RENSSELAER POLYTECHNIC INSTITUTE, Troy, MI (US)

(72) Inventors: Anthony R. D'Amato, Ithaca, NY (US); Nicholas Schaub, Germantown, MD (US); Andrew Sante Fiumara, Fayetteville, NY (US); Paul Michael Troiano, Housatonic, MA (US); Jesus Cardenas, Lake Forest, CA (US); Ryan J. Gilbert, Wynantskill, NY (US)

(73) Assignee: RENSSELAER POLYTECHNIC INSTITUTE, Troy, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/372,165

(22) Filed: Sep. 25, 2023

(65) Prior Publication Data

US 2024/0009312 A1  Jan. 11, 2024

Related U.S. Application Data

(62) Division of application No. 15/766,585, filed as application No. PCT/US2016/055314 on Oct. 4, 2016, now Pat. No. 11,793,877.

(Continued)

(51) Int. Cl.
*A61K 47/34* (2017.01)
*A61K 9/70* (2006.01)
(Continued)

(52) U.S. Cl.
CPC ............ *A61K 47/34* (2013.01); *A61K 9/70* (2013.01); *A61L 15/44* (2013.01); *A61L 27/18* (2013.01);
(Continued)

(58) Field of Classification Search
CPC ........ A61K 47/34; A61K 9/70; A61K 31/455; A61K 2300/00; A61L 15/44; A61L 27/18;
(Continued)

(56) References Cited

U.S. PATENT DOCUMENTS 9,040,069 B2  5/2015  Diener
2001/0051814 A1  12/2001  Shalaby
(Continued)

FOREIGN PATENT DOCUMENTS

CN  104711759 A  6/2015
WO  2002045720 A1  6/2002

OTHER PUBLICATIONS

International Search Report and The Written Opinion of the International Searching Authority, International Application No. PCT/US2016/055314, mailed Jan. 24, 2017.
(Continued)

*Primary Examiner* — Robert A Wax
*Assistant Examiner* — Quanglong N Truong
(74) *Attorney, Agent, or Firm* — Barclay Damon LLP; Anthony P. Gangemi

(57) ABSTRACT

Embodiments of the invention relate generally to electrospun fibers and, more particularly, to the controlled release of an active pharmaceutical ingredient (API) from electrospun fiber scaffolds (EFSs).

5 Claims, 5 Drawing Sheets

Related U.S. Application Data

(60) Provisional application No. 62/237,756, filed on Oct. 6, 2015.

(51) Int. Cl.

| | |
|---|---|
| *A61K 31/455* | (2006.01) |
| *A61L 15/44* | (2006.01) |
| *A61L 27/18* | (2006.01) |
| *A61L 27/54* | (2006.01) |
| *D01D 5/00* | (2006.01) |
| *D01F 1/10* | (2006.01) |
| *D01F 6/62* | (2006.01) |
| *D01F 6/68* | (2006.01) |
| *D02J 13/00* | (2006.01) |
| *D04H 1/728* | (2012.01) |

(52) U.S. Cl.
CPC .............. *A61L 27/54* (2013.01); *D01D 5/003* (2013.01); *D01F 1/10* (2013.01); *D01F 6/625* (2013.01); *D02J 13/00* (2013.01); *D02J 13/003* (2013.01); *D04H 1/728* (2013.01); *A61K 31/455* (2013.01); *A61K 2300/00* (2013.01); *A61L 2300/434* (2013.01); *A61L 2300/602* (2013.01); *D01F 6/68* (2013.01)

(58) Field of Classification Search
CPC .............. A61L 27/54; A61L 2300/434; A61L 2300/602; D01D 5/003; D01F 1/10; D01F 6/625; D01F 6/68; D02J 13/00; D02J 13/003; D04H 1/728; C08L 67/04
See application file for complete search history.

(56) References Cited

U.S. PATENT DOCUMENTS

| | | |
|---|---|---|
| 2008/0220054 A1 | 9/2008 | Shastri et al. |
| 2011/0038936 A1 | 2/2011 | Griswold et al. |
| 2012/0136090 A1 | 5/2012 | Kasuga et al. |
| 2014/0128345 A1 | 5/2014 | Woodrow et al. |

OTHER PUBLICATIONS

Pluta, M., et al., "Plastic Deformation of Amorphous Poly(L/DL-lactide): Structure Evolution and Physical Properties," Biomacromolecules, vol. 8, pp. 1836-1843, 2007.

Sonseca, A., et al., "Electrospinning of biodegradable polylactide/hydroxyapatite nanofibers: Study on the morphology, crystallinity structure and thermal stability," Polymer Degradation and Stability, vol. 97, Issue 10, pp. 2052-2059, 2012.

CONTROLLED DRUG RELEASE FROM
ELECTROSPUN FIBERS

CROSS REFERENCE TO RELATED APPLICATION

This application is a divisional patent application of U.S. Non-Provisional patent application Ser. No. 15/766,585, filed Apr. 6, 2018, which is a national stage patent application filing of International Patent Application No. PCT/US2016/055314, filed Oct. 4, 2016, which claims the benefit of U.S. Provisional patent application Ser. No. 62/237,756, filed Oct. 6, 2015, which are incorporated herein by reference in their entirety, including any figures, tables, and drawings.

STATEMENT REGARDING FEDERALLY-SPONSORED RESEARCH OR DEVELOPMENT

This invention was made with government support under National Science Foundation grants 1150125 and 1358895, as well as New York State Department of Health grant C030239. The government has certain rights in the invention.

BACKGROUND

Electrospun, polymer fibers are nano scale or microscale fibers. The delivery of drugs using electrospun fibers is known. Typically, however, a drug is released from electrospun fibers in a single burst. Not only does this preclude the controlled or prolonged release of the drug, as may be desirable or necessary in the treatment of certain diseases or disorders, but it also increases the likelihood of adverse effects that may be associated with the drug.

Known techniques for altering drug release from electrospun fibers usually involve modifying the drug itself or the polymer molecules used to form the electrospun fibers. This is generally undesirable, since the efficacy of the drug may be altered and/or the polymer molecules may need to be altered differently depending on the drug to be delivered.

BRIEF SUMMARY OF THE INVENTION

One embodiment of the invention provides a controlled-release drug delivery system comprising: an electrospun fiber scaffold (EFS) having a crystallinity percentage greater than zero; and at least one active pharmaceutical ingredient (API), wherein the at least one API is released from the EFS upon administration of the drug delivery system to an individual.

Another embodiment of the invention provides a drug delivery system comprising: a first electrospun fiber scaffold (EFS) having a first crystallinity percentage; a second EFS having a second crystallinity percentage different than that of the first EFS; and at least one active pharmaceutical ingredient (API), wherein the at least one API is released from the first EFS at a first rate and the at least one API is released from the second EFS at a second rate different than the first release rate upon administration of the drug delivery system to an individual. In some embodiments, the drug delivery system includes a crystallinity gradient between the first electrospun fiber scaffold and the second electrospun fiber scaffold.

Still another embodiment of the invention provides a method of preparing a drug delivery device, the method comprising: obtaining a solution including a polymer and an active pharmaceutical ingredient (API) dissolved in a solvent; electrospinning the solution to obtain an electrospun fiber scaffold (EFS); and heating the EFS to increase a crystallinity percentage of the EFS.

BRIEF DESCRIPTION OF THE SEVERAL VIEWS OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION

Applicant has surprisingly found that the rate of release of active pharmaceutical ingredients (APIs) from electrospun fiber scaffolds (EFS) is related to the degree of crystallinity of the EFS. This crystallinity can be altered by heat treating the EFS after electrospinning. According to some embodiments of the invention, such heat treating includes heating the EFS (which includes the API) to a temperature between about 50° C. and about 130° C. for about 60 minutes.

More surprisingly, Applicant has found that while prolongation of the release of 6-aminonicotinamide (6AN) from poly-L-lactic acid (PLLA) fiber scaffolds initially increases with increasing heat treating temperature (and consequently, increasing crystallinity percentage), this prolongation ceases when the heat treating temperature reaches between about 60° C. and about 80° C.

Figure 1:
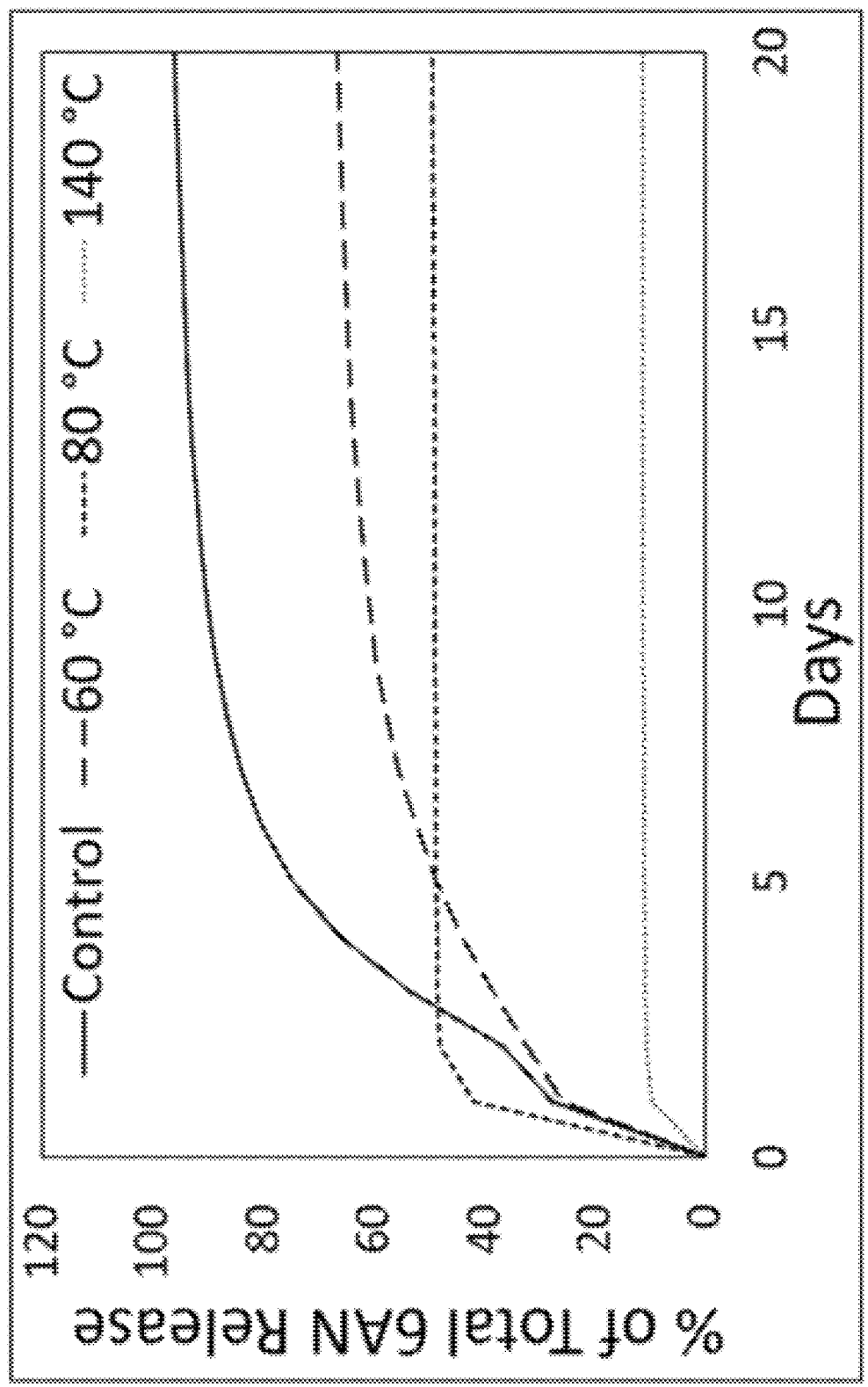
FIG. 1 shows the release of 6-aminonicatinomide (6AN) from electrospun fiber scaffolds (EFSs), including heat-treated EFSs according to embodiments of the invention.

For example, FIG. 1 shows the cumulative release of 6AN from PLLA fiber scaffolds. Control (not heat treated) EFSs show a relatively rapid release of 6AN, such that nearly 100% of the 6AN is released by day 10.

EFSs heat treated to 60° C., on the other hand, exhibited a more gradual release of 6AN such that, at the same day 10, approximately 60% of the 6AN was released. The release of 6AN continued at a lower release rate beyond day 10.

The release of 6AN from EFSs heat treated to 80° C. was more rapid than either the untreated or 60° C. treated EFSs, releasing over 40% of the 6AN on day 1. However, total 6AN release plateaued at about 50% by day 2, with no 6AN release after about day 2.

This difference in 6AN release rates allows for the provision of drug delivery profiles tailored to the parameters of the API employed and the condition or patient to be treated. For example, where a particular patient or condition calls for a large initial dose of an API followed by a prolonged, lower dose of the API, a patient may be simultaneously administered EFSs heat treated to different temperatures, wherein a first temperature is operable to promote a high initial release of the API and a second temperature is operable to promote a prolonged release of the API. Referring again to FIG. 1, for example, a patient may be simultaneously administered EFSs heat treated to about 80° C. and EFSs heat treated to about 60° C. This would facilitate the release of a large dose of 6AN (via the 80° C.-treated EFSs), as well as a prolonged release of a lower dose of 6AN (via the 60° C.-treated EFSs) over subsequent days.

Figure 2:
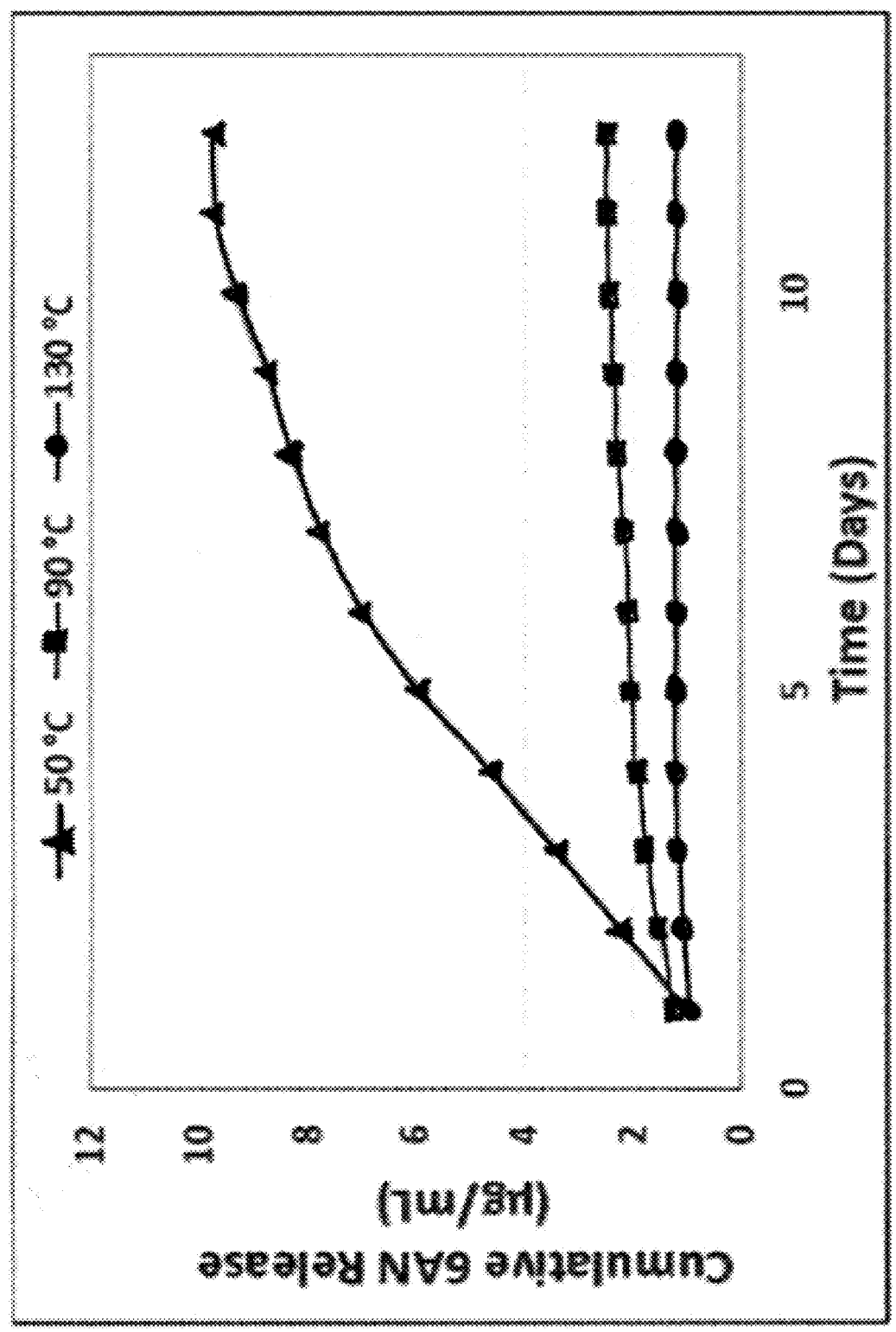
FIG. 2 shows 6AN release profiles according to various embodiments of the invention.

FIG. 2 shows similar release profiles for EFSs heat-treated to 50° C., 90° C., and 130° C., with the cumulative release of 6AN shown in µg/mL. Here, 50° C.-treated EFSs exhibited a markedly prolonged and more extensive release of 6AN than did either the 90° C.- or 130° C.-treated EFSs.

The prolonged, sustained release achievable using, for example, the 50° C.-treated EFSs may reduce undesirable effects of an API being delivered. For example, the 50° C.-treated EFS in FIG. 2 may reduce astrocyte reactivity, a known consequence of the use of 6AN in the treatment of spinal cord injuries.

Figure 3:
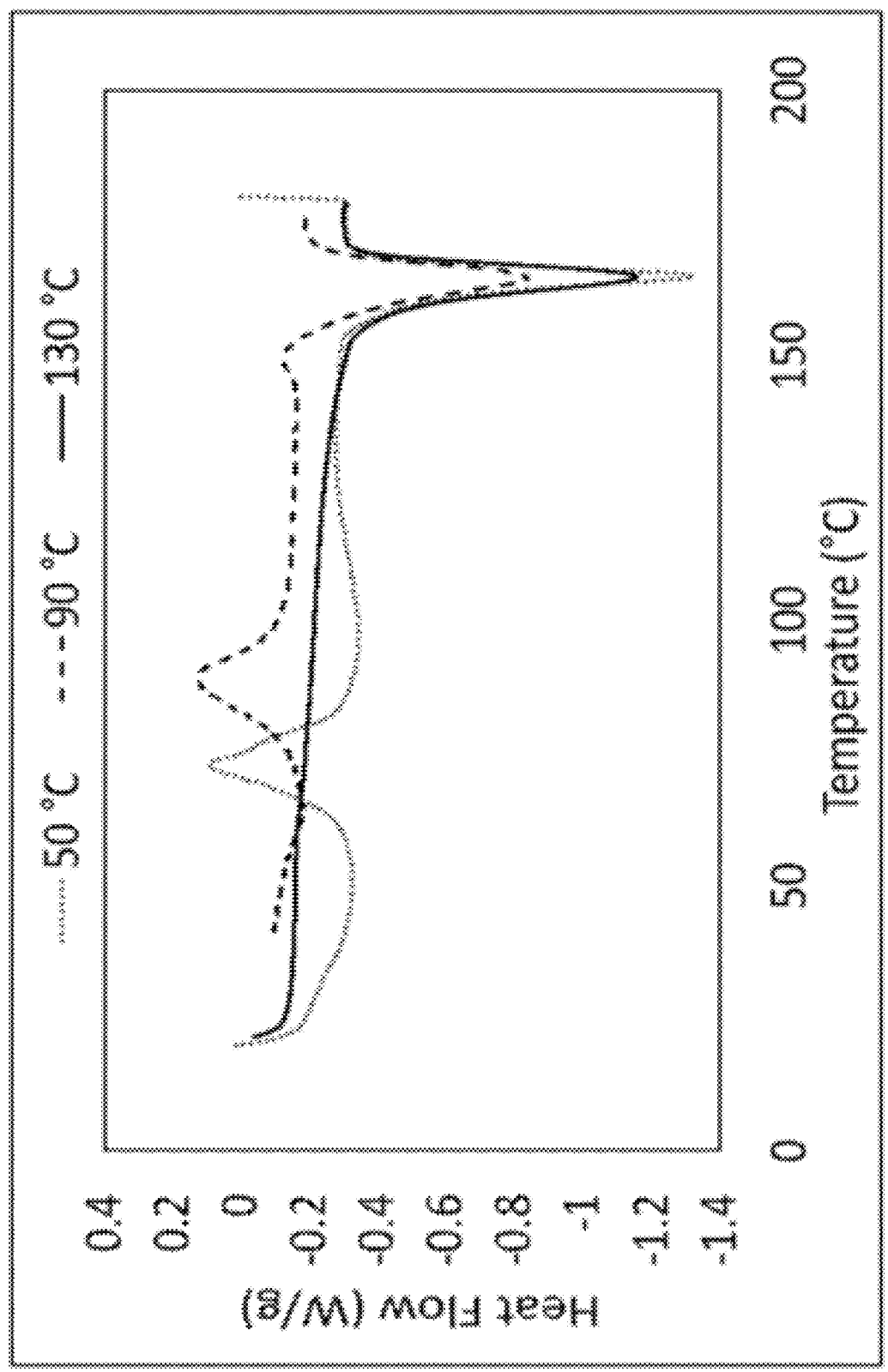
FIG. 3 shows differential scanning calorimetry (DSC) profiles for the EFSs of FIG. 2.

FIG. 3 shows differential scanning calorimetry (DSC) profiles for the EFSs of FIG. 2, which were used to assess the degree of crystallinity of each EFS. FIG. 3 shows the differences in energy required to fully crystallize the EFSs. The polymer crystallinities calculated from the DSC results in FIG. 3 were 13.3%, 25.6%, and 100%, respectively, for the 50° C.-, 90° C.-, and 130° C.-treated EFSs.

Embodiments of the invention result in useful crystallinity percentages between about 10% and about 25%, typically between about 10% and about 15%, for the release of 6AN. These crystallinities will be different for other APIs, however, as would be recognized by one skilled in the art. As such, more generally, useful crystallinity percentages will range from about 5% to about 90%, or from about 10% to about 80%, or from about 15% to about 70%, or from about 20% to about 60%. The particular crystallinity percentages useful in the administration of a particular API would be readily determinable by one of ordinary skill in the art.

Figure 4:
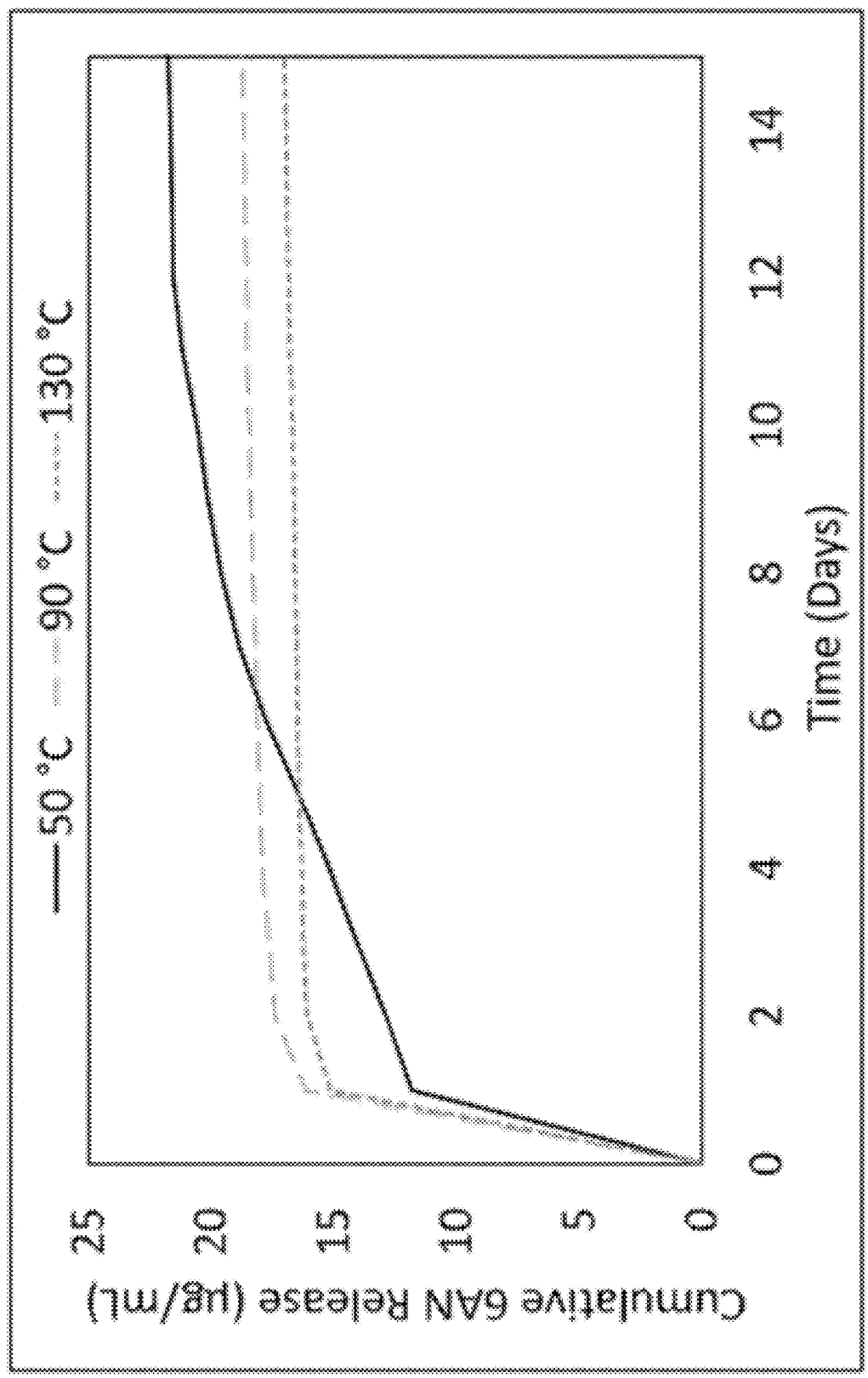
FIG. 4 shows 6AN release profiles according to other embodiments of the invention.

FIG. 4 shows the release profiles for EFSs loaded with a higher dose of 6AN than the EFSs shown in FIG. 2. As can be seen, the initial release from 90° C.- and 130° C.-treated EFSs is more rapid, but quickly plateaus at about day 2. Release from 50° C.-treated EFSs is initially slower, but continues to increase until about day 12.

Methods according to embodiments of the invention generally comprise heating electrospun fibers on a heat source such as a hot plate for a period of about an hour. According to one embodiment of the invention, a solution containing 240 mg of PPLA and 24.0 mg of 6AN in 2.0 g of 1,1,1,3,3,3-hexafluoro-2-propanol were electrospun using a 5 cm needle-collection disc gap at 1000 rpm, a 2 mL/h solution flow rate, 10 kV, and a relative humidity of 30-35%. Variations in these parameters are possible, of course, as will be apparent to one skilled in the art.

Electrospun fiber scaffolds obtained using the method above were then heated on a hot plate for about one hour at temperatures ranging from 50° C. to 130° C. This has the effect, as explained above, of increasing the polymer crystallinity of the EFSs, thereby altering the release profile of the 6AN from the EFSs. Release of 6AN from the EFSs described above was measured by submerging the EFSs in phosphate-buffered saline (PBS) and measuring absorbance at 264 nm.

Other methods according to the invention are possible, of course. For example, rather than heating on a hot plate, Applicant employed an alternative method of altering polymer crystallinity of an EFS. According to this alternative method, EFSs were heat-treated in a standard laboratory incubator, again for about an hour.

Both relative humidity and carbon dioxide percentage in the incubator were higher (50% or more and 5% or more, respectively) than in the hot plate treatment described above. This, Applicant believes, gave rise to a unique and unexpected biphasic release profile shown in FIG. 5. Here, it can be seen that 6AN is initially released at a relatively rapid rate until about day 2, after which the release rate is much more gradual until about day 8. From there, the 6AN release rate increases again until about day 12, followed by a more gradual decrease in release rate than observed at the first plateau.

Figure 5:
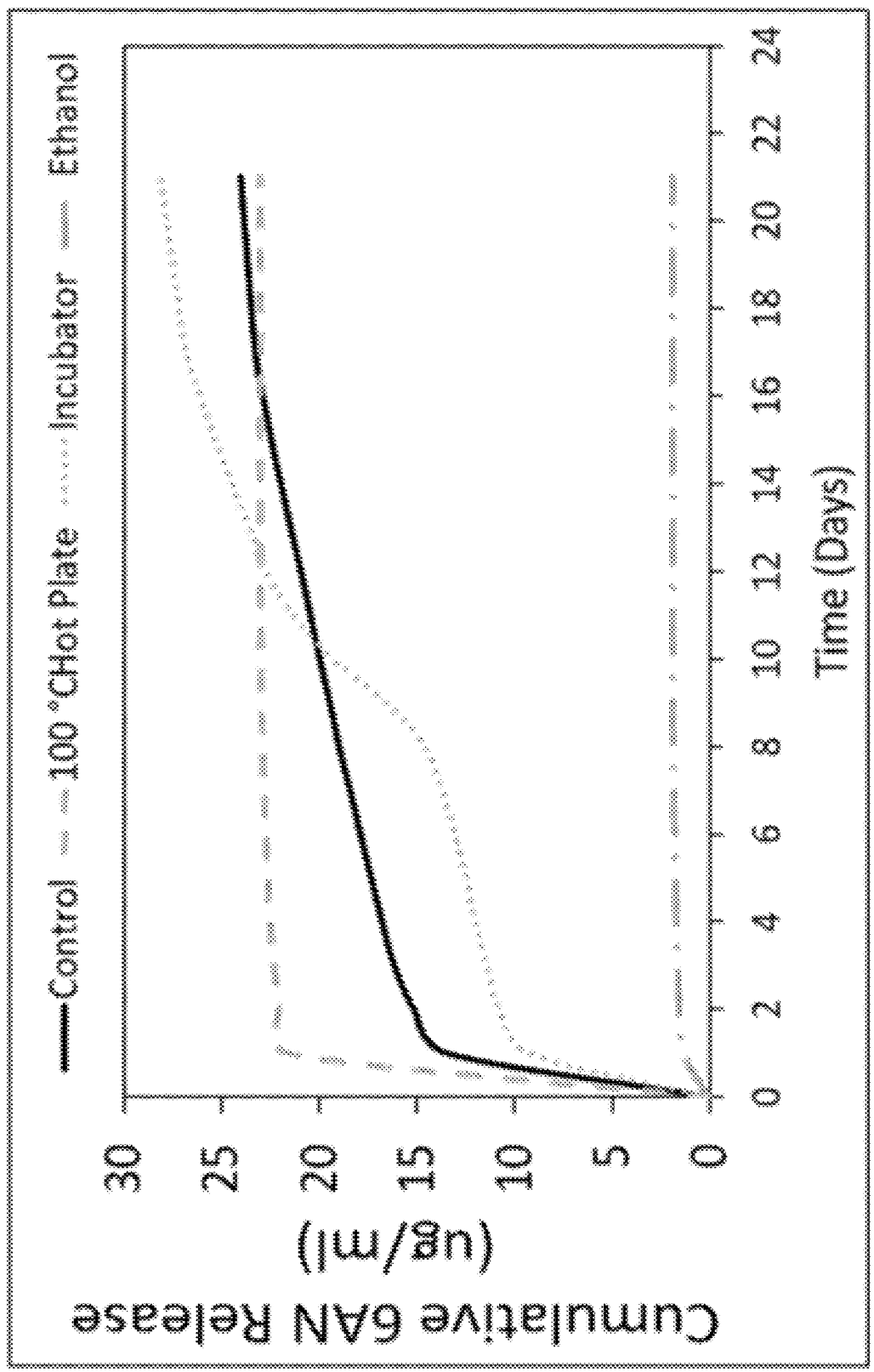
FIG. 5 shows a biphasic 6AN release profile according to yet another embodiment of the invention.

The release profile seen in FIG. 5 may be particularly useful, for example, in the treatment of a disease or condition for which an initial, rapid release of an API, followed by a further, delayed release of the API. One skilled in the art will recognize any number of such diseases or conditions and any number of APIs for which such a release profile may be desirable.

The various embodiments of the invention described herein comprise PLLA fiber scaffolds for use in releasing 6AN. This, of course, is neither necessary nor essential, as will be recognized by one skilled in the art.

Poly(lactic acid) (PLA) is a commonly-used, biodegradable, thermoplastic, aliphatic polyester, derivable from natural sources, such as corn starch. PLLA is its L-enantiomer, with a glass transition temperature between 60° C. and 65° C. Other polymers may be employed, of course, to prepare EFSs suitable for use in practicing embodiments of the invention, provided such polymers are capable of crystallization.

6AN is an NADP+ inhibitor of 6-phosphogluconate dehydrogenase and has been used to enhance the cytotoxicity of cisplatin in the treatment of cancers. Other APIs may be employed, of course, in practicing embodiments of the invention, provided such APIs are capable of release from EFSs.

The use of PLLA and 6AN in the examples described herein is merely for purposes of illustration and explanation and should not be viewed as limiting the scope of the invention.

This written description uses examples to disclose the invention, including the best mode, and also to enable any person skilled in the art to practice the invention, including making and using any devices or systems and performing any related or incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of preparing a drug delivery device, the method comprising: obtaining a solution including poly-L-lactic acid (PLLA) and at least one active pharmaceutical ingredient (API) dissolved in a solvent; electrospinning the solution to obtain a first PLLA electrospun fiber scaffold (EFS); electrospinning the solution to obtain a second PLLA EFS; heat treating the first EFS at a first temperature; and heat treating the second EFS at a second temperature, wherein the first temperature is between about 50° C. and about 60° C., and the second temperature is at least 80° C.

2. The method of claim 1, wherein heat treating the first EFS or heat treating the second EFS includes heat treating at a relative humidity of 50% or more in the presence of 5% or more carbon dioxide.

3. The method of claim 1, wherein the at least one API includes 6-aminonicotinamide (6AN).

4. The method of claim 1, wherein the at least one API includes a plurality of APIs.

5. The method of claim 1, further comprising a crystallinity gradient between the first PLLA EFS and the second PLLA EFS.

* * * * *